United States Patent [19]

Rolfe

[11] 4,176,659

[45] Dec. 4, 1979

[54] CATHETER WITH MEASUREMENT ELECTRODES

[76] Inventor: Peter Rolfe, 9, Henwood Dr., Boars Hill, Oxford, England

[21] Appl. No.: 816,950

[22] Filed: Jul. 19, 1977

[30] Foreign Application Priority Data

Jul. 21, 1976 [GB] United Kingdom ............... 30288/76

[51] Int. Cl.² .............................................. A61B 5/00
[52] U.S. Cl. .................................. 128/635; 204/195 B
[58] Field of Search .................... 128/2 E, 2.1 E, 404, 128/418, 419 P; 204/195 B, 195 P

[56] References Cited

U.S. PATENT DOCUMENTS

| | | | |
|---|---|---|---|
| 3,682,159 | 8/1972 | Imredy et al. | 128/2 E |
| 3,729,008 | 4/1973 | Berkovits | 128/418 |
| 3,878,830 | 4/1975 | Bicher | 128/2 E |
| 4,020,830 | 5/1977 | Johnson et al. | 128/2 E |
| 4,041,933 | 8/1977 | Reichenberger | 128/2 E |

OTHER PUBLICATIONS

Kakiuchi et al., "A Fast Responding Catheter Tip . . . .Calibrater," Bull. Res. Inst. Appl. Elec., Japan, vol. 27, No. 3-4, Dec. 1975, pp. 17-24.

Primary Examiner—LeeS. Cohen
Attorney, Agent, or Firm—Larson, Taylor & Hinds

[57] ABSTRACT

A catheter is provided which comprises a tubular body that defines a passage therewithin terminating in an axially-facing opening at the tip end of the catheter, the opening serving as a sampling port. A pair of annular electrodes are arranged in spaced relationship around the sampling port on the rim of the open end and are connected to suitable measuring equipment.

8 Claims, 3 Drawing Figures

CATHETER WITH MEASUREMENT ELECTRODES

The present invention relates to catheters, more particularly to those which are designed for measuring the concentration of gases, ions or molecules dissolved or otherwise contained, in liquid or gaseous media. Examples of such catheters may be in the form of polarographic oxygen sensors, hydrogen ion measuring electrode systems (e.g. glass pH electrodes), carbon dioxide electrodes, or input devices for use with mass spectrometers. Such forms of apparatus may be used for measurements in a variety of media, including blood both in vivo and in vitro. It is desirable that such apparatus for use in vivo takes into account the possibility of clotting and other related adverse phenomena; some forms of in vivo sensors are not ideal in this respect.

DETAILED DESCRIPTION OF THE DRAWINGS

Figure 1:
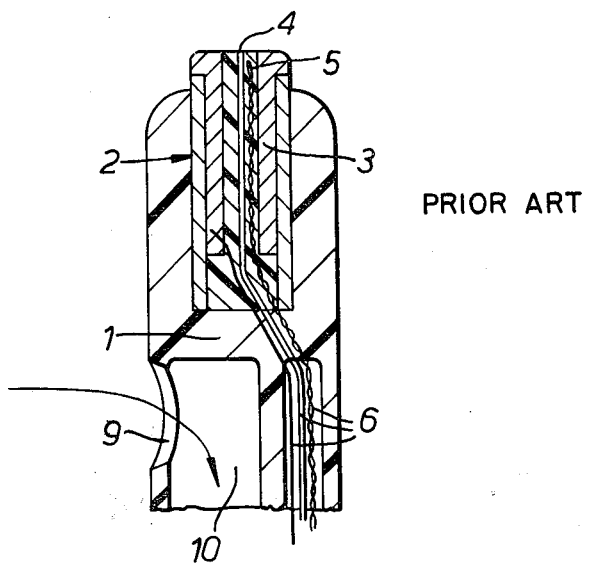
FIG. 1 shows an axial sectional view of a prior art catheter.

Reference will now be made to FIG. 1 of the accompanying drawings, which shows an axial sectional view of the proximal end of a catheter which does not embody the present invention. The catheter is designed for in vivo measurements. An electrochemical oxygen sensor 2 is positioned in the tip of a plastics (poly vinyl chloride) catheter 1 which may be inserted into a blood vessel, the catheter being about 1.7 mm in diameter at its proximal end. Electrical connecting wires 6 from the sensor anode 3, cathode 4 and integral thermocouple 5 pass down the catheter to a plug or socket, and blood may be withdrawn via a laterally positioned sampling port 9, and thence along lumen 10, as indicated by the arrow. This blood withdrawing facility is very important both with the catheter illustrated in FIG. 1 and with other forms of catheter, unfortunatly, however, blockage of the sampling lumen with thrombus is a recurring problem. The tendency for clotting to occur may be minimized by ensuring a high quality surface finish on the catheter, and by filling the lumen with heparin containing fluids between blood sampling. Nevertheless, clotting may still occur and is found to be more likely in catheters having lateral sampling ports.

According to the present invention, there is provided a catheter comprising a tubular portion which has an open end, to provide a sampling port at the tip of the catheter, and two annular electrodes provided on the rim of the said open end, around the sampling port.

It is possible to modify the catheter illustrated in FIG. 1 so that it incorporates the features of the present invention.

Figures 2A, 2B:
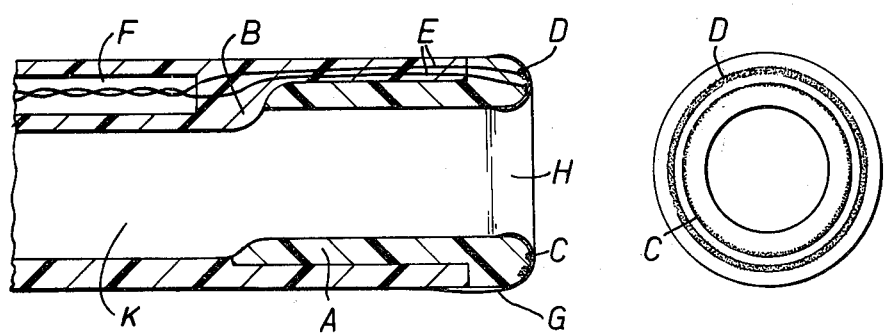
FIGS. 2a and 2b show respectively an axial sectional view and an axial end view of a catheter which embodies the present invention.

Reference will now be made, by way of example, to FIGS. 2(a) and 2(b) of the accompanying drawings, which show respectively an axial sectional view and an end view, both drawn to scale, of the proximal end of a catheter which embodies the present invention. The catheter is provided at its proximal end with a rigid poly vinyl chloride container or tubular end portion A, part of which is fitted coaxially within an end part of a main elongate tubular plasticised poly vinyl chloride body or part B of the catheter, which part has an outside diameter of 1.67 mm. The assembly of the tubular end portion A and main elongate tubular part B is referred to hereinafter as a tubular body. Two annular electrodes C and D, constituted by rings of silver, are vacuum deposited or otherwise attached to the rim at the open end of the cylinder end portion A, the centres of the electrodes lying on the axis of the cylinder and the electrodes being the cathode and anode respectively when the catheter is in use. Connecting conductors E extend from these silver rings through the body B of the catheter, and thence along an additional lumen F of the catheter to a terminating plug or socket. A gas diffusion membrane G and an electrolyte cover the rim, including the two electrodes C and D. Blood may be withdrawn via a sampling port H defined at the tip of the catheter by the rim of the cylinder A, and thence through the main lumen K of the catheter.

The catheter illustrated in FIG. 2 is an oxygen concentration measuring device for intra-arterial use.

What is claimed is:

1. A catheter comprising a tubular body which defines therewithin a passage which extends to an axially-facing open end of the tubular body and which serves as a sampling port at the tip of the catheter, said catheter further comprising first and second annular electrodes which are arranged in spaced relationship on the rim of the said open end around the sampling port, and electrical connection means for connecting said first and second electrodes to measuring equipment.

2. A catheter as claimed in claim 1, wherein an end portion of the tubular body which includes the tip of the catheter comprises poly vinyl chloride.

3. A catheter as claimed in claim 1, wherein the said first and second annular electrodes are vacuum deposited on the said rim.

4. A catheter as claimed in claim 1, wherein the said electrodes comprise silver.

5. A catheter as claimed in claim 1, wherein the tubular body comprises a main elongate tubular part and tubular end portion secured to said tubular part, said tubular end portion including the tip of the catheter.

6. A catheter as claimed in claim 5, wherein part of the said tubular end portion fits coaxially within an end portion of the said main elongate tubular part.

7. A catheter as claimed in claim 1, wherein the said rim, including the first and second annular electrodes, is covered by a gas diffusion membrane.

8. A catheter as claimed in claim 1, wherein the said rim, including the first and second annular electrodes, is covered by an electrolytic material.

* * * * *